(12) United States Patent
Stone

(10) Patent No.: US 6,312,443 B1
(45) Date of Patent: Nov. 6, 2001

(54) EXPANDABLE CANNULA

(75) Inventor: Corbett W. Stone, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

(21) Appl. No.: 09/467,944

(22) Filed: Dec. 21, 1999

Related U.S. Application Data

(60) Provisional application No. 60/113,651, filed on Dec. 23, 1998.

(51) Int. Cl.[7] ................................................. A61M 29/00
(52) U.S. Cl. ............................................. 606/198; 623/1.1
(58) Field of Search .................................. 606/198, 190; 604/272, 104, 103.06, 103.14, 106, 107, 164.03, 239, 264; 600/204, 115

(56) References Cited

U.S. PATENT DOCUMENTS

| | | | |
|---|---|---|---|
| 4,141,364 | * | 2/1979 | Schultze ........................ 128/207.15 |
| 4,601,713 | * | 7/1986 | Fuqua ................................... 604/514 |
| 5,158,545 | * | 10/1992 | Trudell et al. ....................... 604/509 |
| 5,176,659 | * | 1/1993 | Mancini ............................... 604/523 |
| 5,395,349 | * | 3/1995 | Quiachon et al. .................. 604/248 |
| 5,718,693 | * | 2/1998 | Gupta ................................... 604/264 |
| 5,762,604 | * | 6/1998 | Kieturakis ........................... 600/115 |
| 5,797,951 | * | 8/1998 | Mueller ............................... 606/198 |

* cited by examiner

*Primary Examiner*—Kennedy Schaetzle
*Assistant Examiner*—Kristen Droesch
(74) *Attorney, Agent, or Firm*—Townsend and Townsend and Crew LLP

(57) ABSTRACT

An expandable cannula having a plurality of wall surfaces, the wall surfaces being foldable together one over another such that the cannula assumes a first cross sectional area, and the wall surfaces being unfoldable such that the cannula assumes a second cross sectional area, wherein the first cross sectional area is smaller than the second cross sectional area.

1 Claim, 14 Drawing Sheets

EXPANDABLE CANNULA

CROSS-REFERENCES TO RELATED APPLICATIONS

The present application is a regular patent application of and claims the benefit of priority from U.S. patent application Ser. No. 60/113,651 filed Dec. 23, 1998, the full disclosure of which is incorporated herein by reference.

TECHNICAL FIELD

The present invention relates to surgical cannulae.

SUMMARY OF THE INVENTION

The present invention provides an expandable surgical cannula which can be inserted into a patient in an initially folded up state and then subsequently unfolded to assume a larger diameter to provide an enlarged access portal for the insertion of surgical instruments therethrough subsequent to cannula insertion into a patient's body. In a preferred aspect, the diameter of the cannula is increased in size by an obturator passing therethrough.

In a preferred aspect, the present expandable cannula comprises a plurality of generally planar longitudinally extending wall sections which are pivotally joined together along their lengths to enclose a cannulated passageway, with at least some of the wall sections being foldable one over another such that the cannula has a first cross sectional area when the wall sections are folded one over another and such that the cannula has a second cross sectional area when the wall sections are unfolded, wherein the first cross sectional area is smaller than the second cross sectional area.

In optional preferred aspects, systems are provided for locking the cannula into an open unfolded state such that the large diameter passageway therethrough is kept open during surgery.

In alternate preferred aspects, the present expandable cannula comprises a plurality of separate overlapping generally planar, (or slightly curved), longitudinally extending wall sections which are disposed within an elastic sheath, wherein the generally planar longitudinally extending wall sections are initially deployed overlapping one another, with at least some of the wall sections disposed on top of adjacent wall sections at one side, and beneath an opposite wall section, at on opposite side when the cannula is unexpanded; and wherein at least some of the wall sections are positioned with their longitudinally extending sides buttressing against one another around the circumference of the cannula after the cannula has been expanded.

BEST MODES OF CARRYING OUT THE INVENTION

Referring to attached FIGS. 1 to 4, an expandable cannula 15 is provided. Cannula 15 is preferably formed from a continuous extrusion of polymeric material with the wall thickness of the polymeric extrusion varying around the circumference of the cannula so as to provide longitudinally extending hinges formed between each of a plurality of generally planar longitudinally extending wall sections. As such, cannula 15 is formed by a plurality of generally planar longitudinally extending wall sections which are pivotally joined together, (and folded one over another), along their lengths to enclose a cannulated passageway 60.

In an exemplary aspect, cannula 15 has sixteen generally planar wall sections, (being wall sections 20, 21, 22, 23, 30, 31, 32, 33, 40, 41, 42, 43, 50, 51, 52, and 53), which are pivotally joined together as shown. It is to be understood that more or less than the presently illustrated sixteen side walls can be used in the present system, keeping within the scope of the present invention.

Figure 1A:
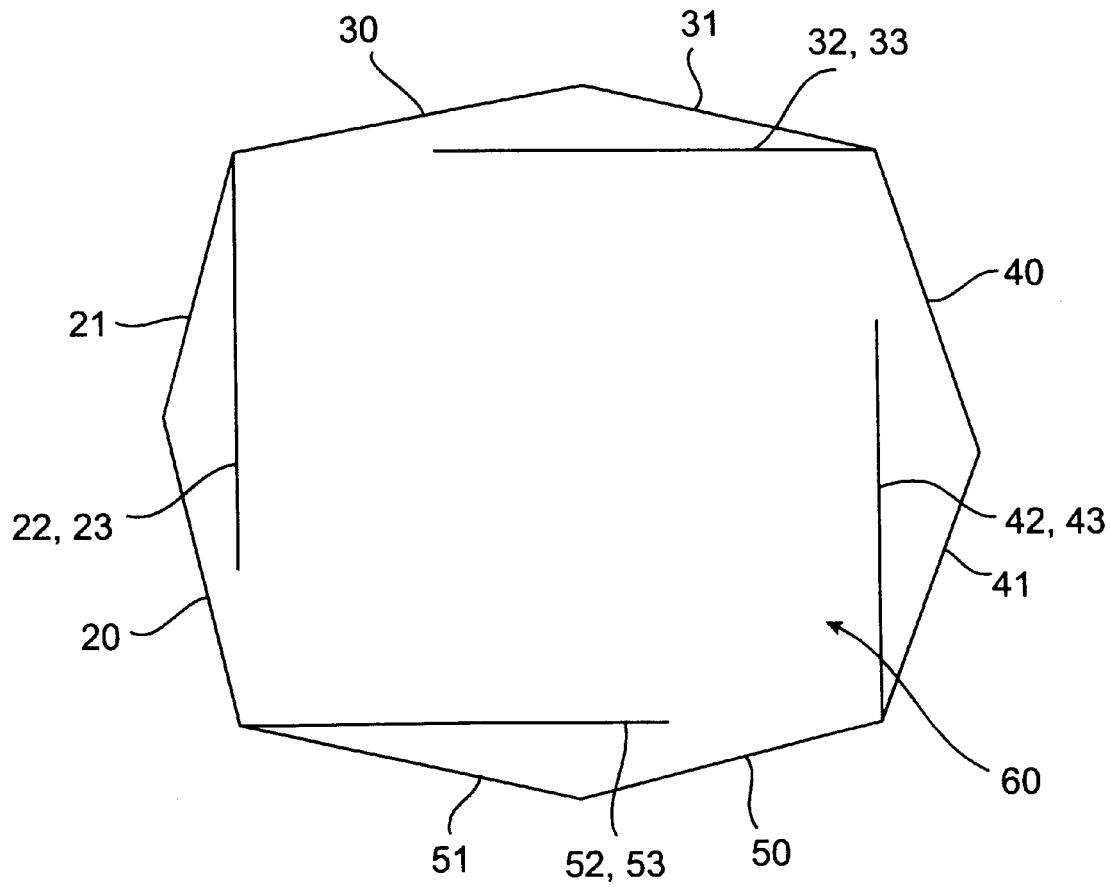
FIG. 1A is a cross-sectional view of a first embodiment of the present cannula folded together in an unexpanded octagonal shape.
Figure 2A:
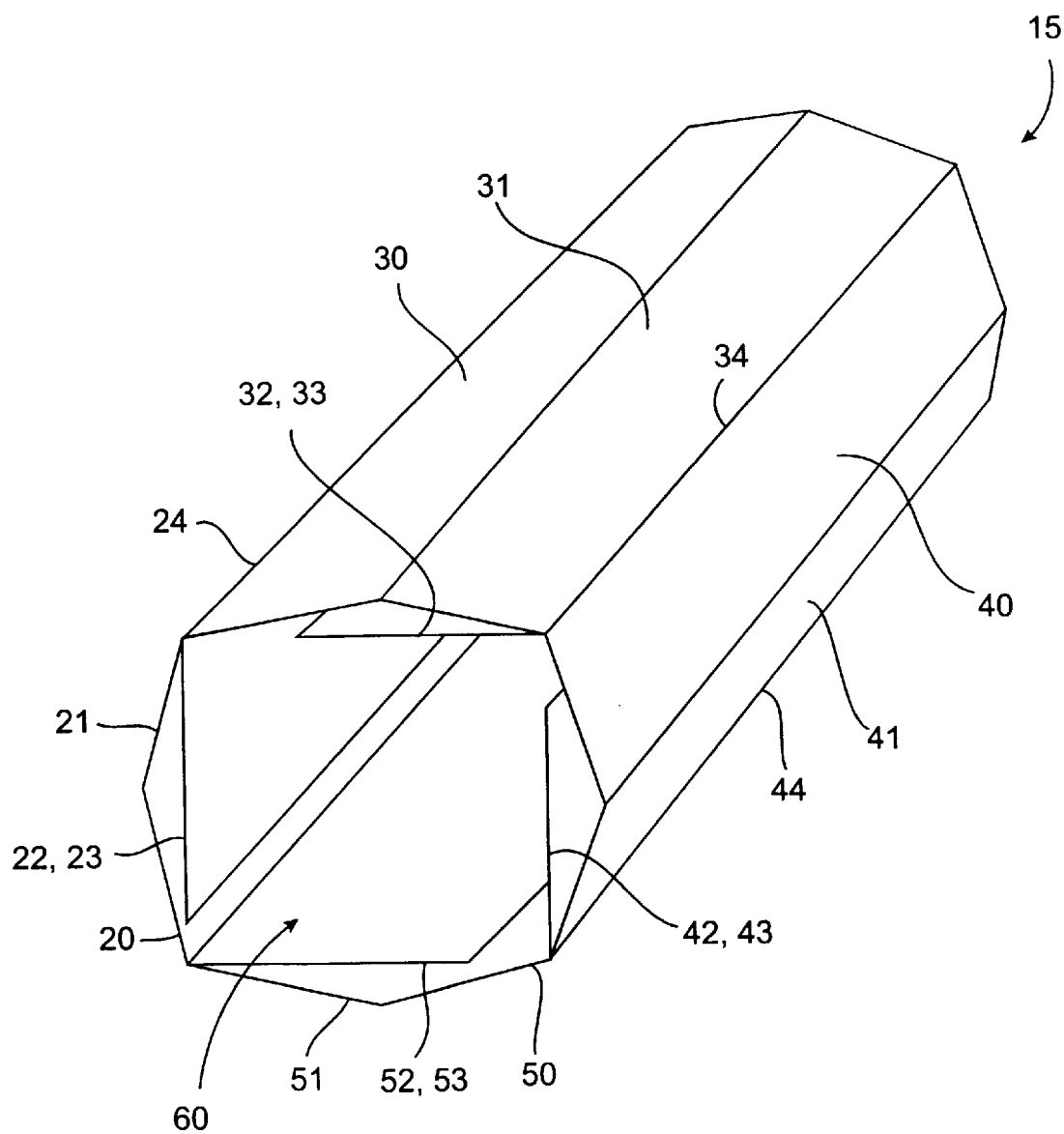
FIG. 2A is a perspective view corresponding to FIG. 1A., showing a portion of the length of the cannula.

When initially inserted into the patient, cannula 15 is folded together to have a compact polygonal shape, (for example, the octagonal shape as is shown in FIGS. 1A and 2A). Continuing with the present example, when folded together, eight outer wall sections 20, 21, 30, 31, 48, 41, 50 and 51 will define an outer surface of cannula 15.

Figure 3:
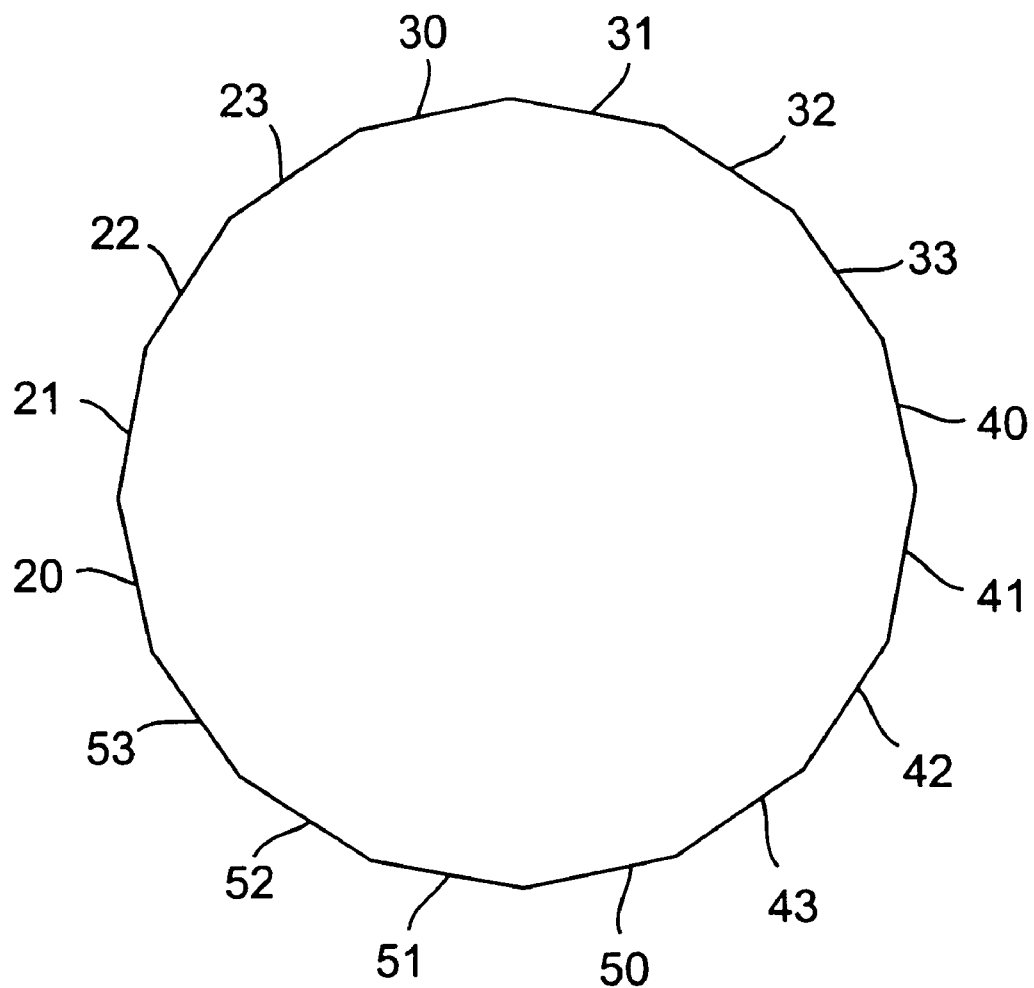
FIG. 3 is a cross-sectional view of the first embodiment of the present cannula unfolded to a fully expanded state.
Figure 4:
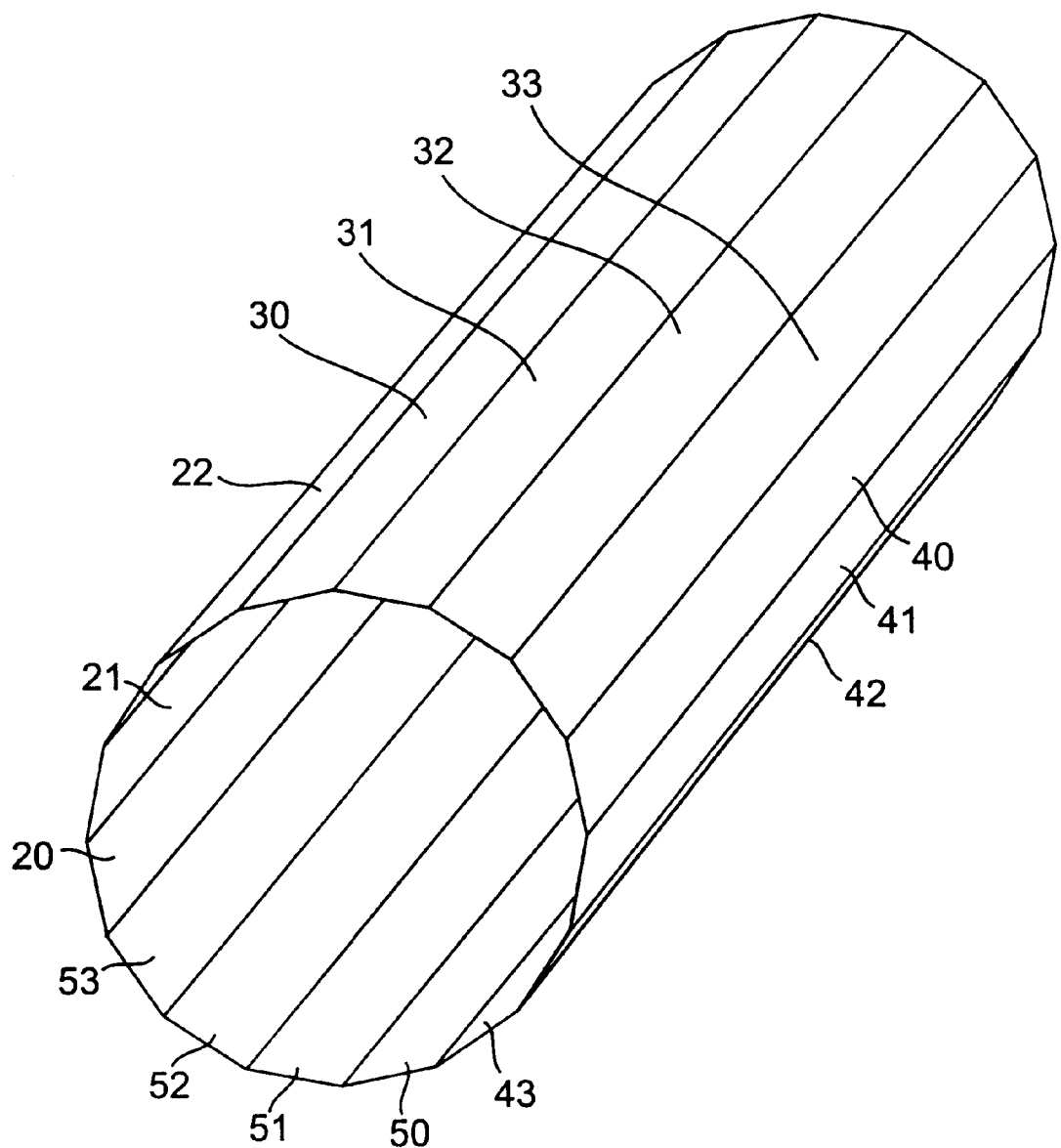
FIG. 4 is a perspective view corresponding to FIG. 3., showing a portion of the length of the cannula.

After insertion into the patient, cannula 15 is then expanded, (as shown in FIGS. 3 and 4) with wall sections 20, 21, 22, 23, 30, 31, 32, 33, 40, 41, 42, 43, 50, 51, 52, and 53 unfolding to define a continuous outer surface which encloses the central longitudinally extending passageway 60 therethrough.

In this aspect of the invention, a plurality of longitudinally extending hinges are formed between each of the adjacent wall sections. (For clarity, only hinges 24, 34, 44 and 54 are numbered). Hinges, (including hinges 24, 34, 44 and 54), may preferably be formed by reducing the wall thickness of the polymer extrusion along these locations such any bending occurs along the longitudinally extending hinges, with the wall sections spanning between the hinges remaining generally planar. Being thicker than the hinges, the wall sections will thus tend to remain planar, (or to remain slightly curved), such that the cannula can initially be folded together before it is expanded.

Figure 5:
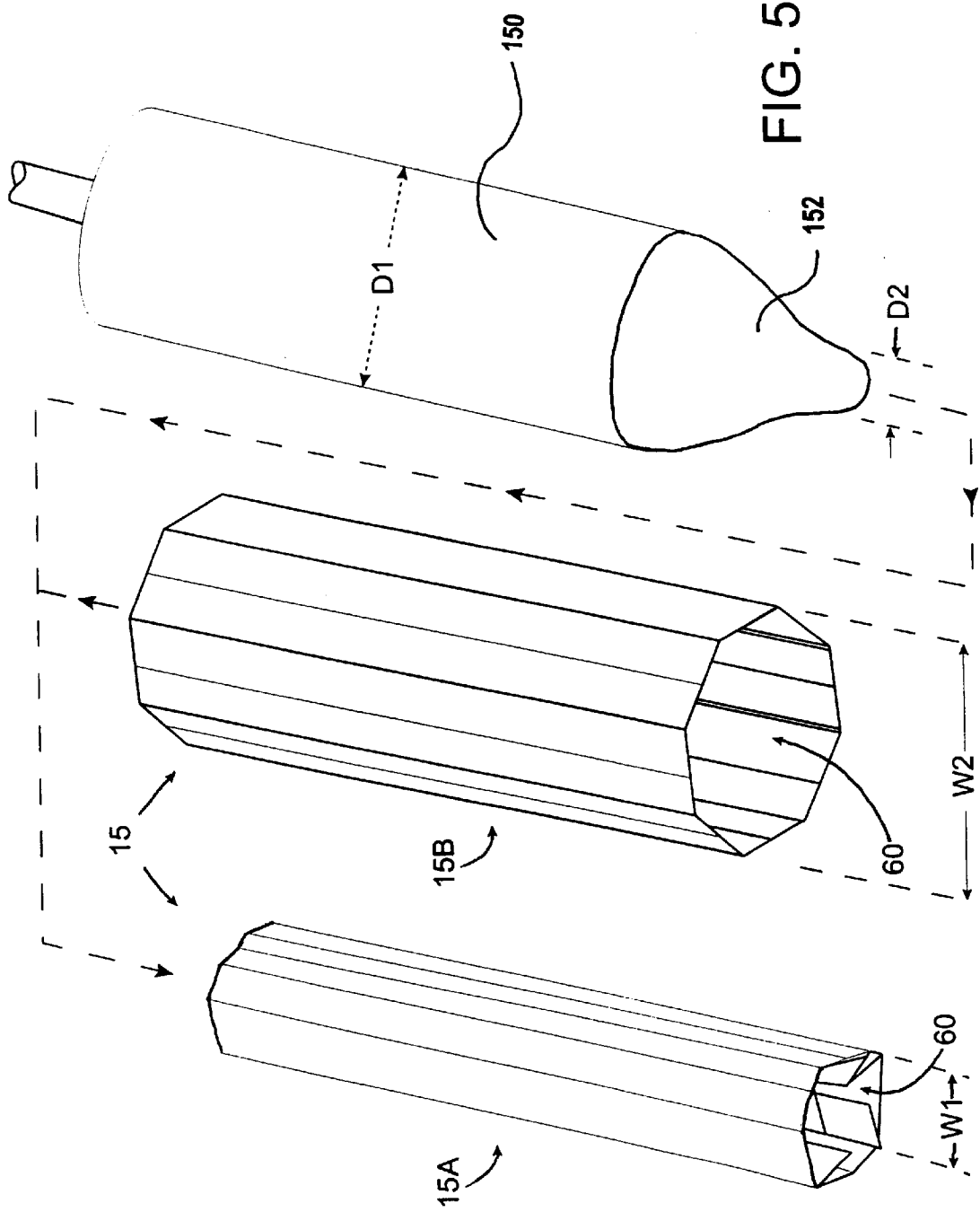
FIG. 5 is a perspective view of a portion of the length of the first embodiment of the present cannula showing comparative dimensions of the cannula in a folded together, unexpanded octagonal shape, and in an unfolded, fully expanded state, with the obturator used for unfolding the cannula.

FIG. 5 illustrates the expansion of cannula 15 from a "folded up" to an "unfolded" state, as follows. Cannula 15 is initially folded together in an octagonal shape (as illustrated by portion 15A of cannula 15). The insertion of an obturator 150 into the longitudinally extending passageway 60 of cannula portion 15A is used to pry open cannula 15 to the final fully expanded state (as illustrated by portion 15B of cannula 15).

As can be seen, cannula portion 15A corresponds to the unexpanded position of the cannula as shown in FIG. 2A and cannula portion 15B corresponds to the expanded position of the cannula as shown in FIG. 4.

As obturator 150 is inserted through passageway 60, its diameter D1, (which is larger that the width W1 of cannula 15 is its initial folded up state (15A), will cause cannula 15 to expand to a final fully expanded state (15B), having a width W2. As such, obturator 150 is preferably dimensioned as a cylinder having a diameter D1 being greater than minimum diameter width W1 of folded up cannula portion 15A and less than maximum diameter W2 of the fully expanded cannula portion 15B.

Subsequent to expansion of cannula 15 to the state illustrated by cannula portion 15B, obturator 150 may then be withdrawn from central passageway 60 such that an enlarged passageway is created having a larger cross sectional area from that of folded up cannula portion 15A.

Figure 1B:
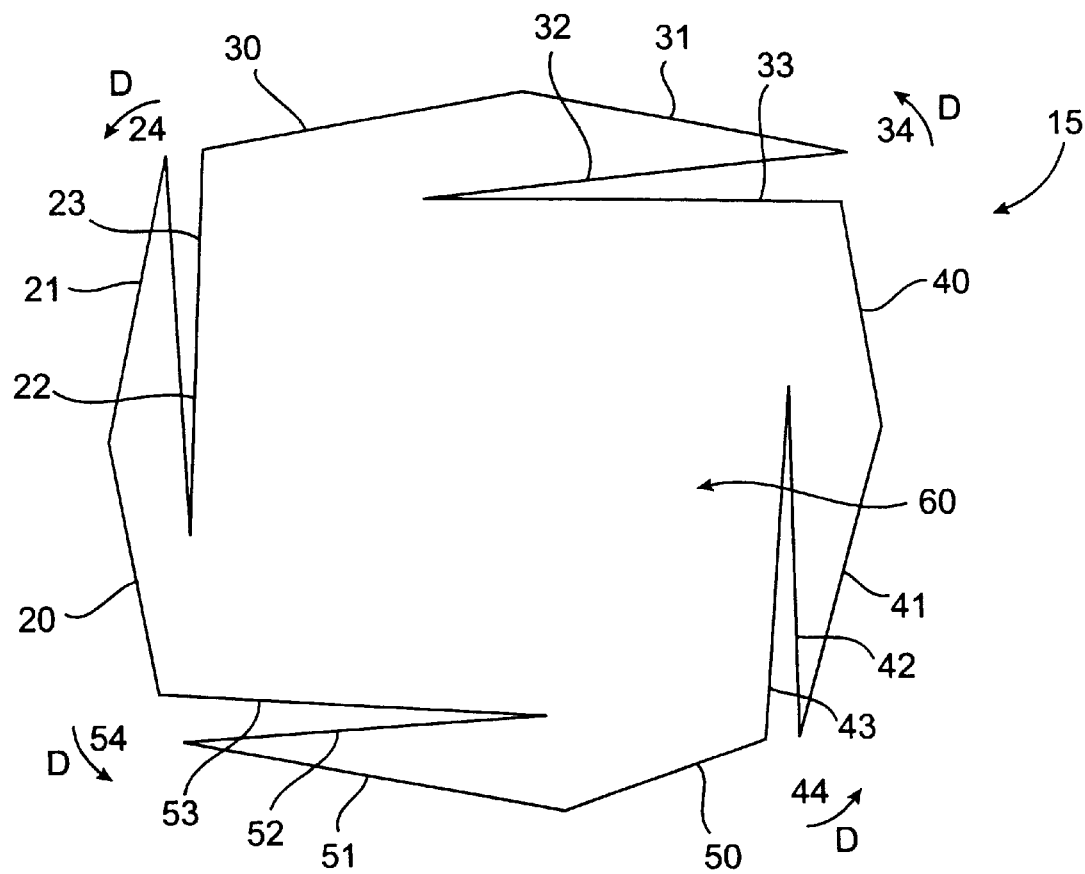
FIG. 1B is a cross-sectional view of the present cannula in a partially unfolded shape.
Figure 2B:
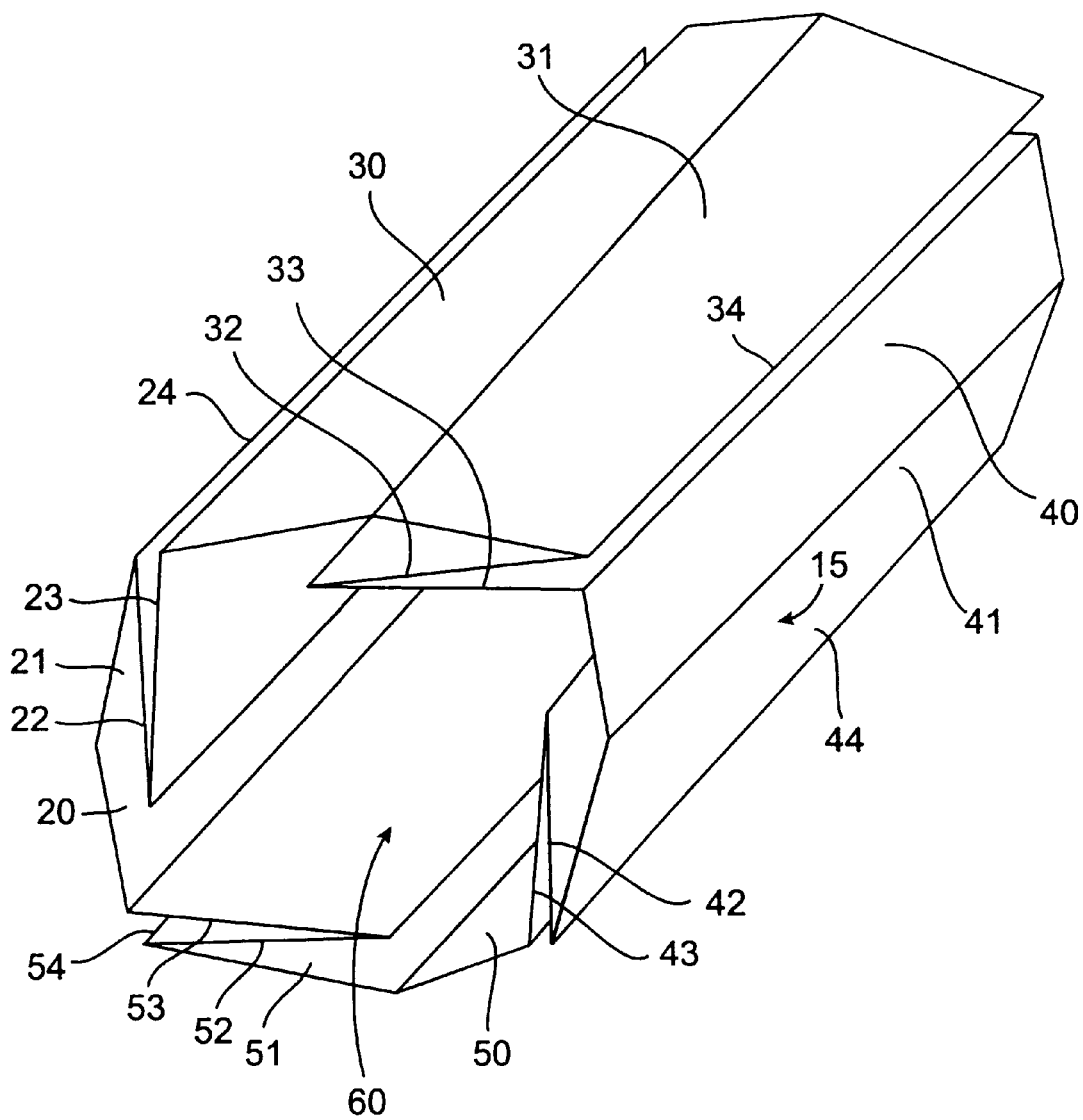
FIG. 2B is a perspective view corresponding to FIG. 1B., showing a portion of the length of the cannula.

As cannula 15 expands from the unexpanded rectangular shape shown in FIGS. 1A and 2A to the fully expanded shape shown in FIGS. 3 and 4, hinges 24, 34, 44 and 54 will move in directions D, as shown by the intermediate position of FIGS. 1B and 2B, such that cannula 15 unfolds.

Obturator 150 preferably has an optional narrow end 152 which has a diameter D2 sufficiently narrow to access passageway 60 when the cannula is unexpanded in the "folded up" state shown as cannula portion 15A. (i.e.: diameter D2 is less than width W1).

Modification and variation of the present invention can be accomplished without departing from the scope of the invention. For example, various numbers of wall sections may be used for any of the cannula embodiments set forth herein. In addition, the wall sections may be generally planar or slightly curved. Moreover, the obturator used to open the cannula need not be cylindrical in shape. Rather, other shapes of the obturator can be used, provided only that the obturator is sufficiently narrow to be received within the narrow folded state of the cannula and sufficiently wide to cause the cannula to unfold as it is inserted. Other systems such as a long balloon (not shown) received within passageway 60 can be inflated to "open" cannula 15 from its initial folded up state to a fully expanded (larger diameter) state.

In additional aspects of the invention, obturator 150 may be received within a tubular sleeve (not shown), and the tubular sleeve may preferably be left behind within cannula 15 to hold cannula 15 in a fully open and unfolded orientation after obturator 150 has been removed. In this aspect of the invention, the tubular sleeve is received over obturator 150, and within cannula 15, and will remain in place to provide a cannulated access after obturator 150 has been removed.

Figure 6A:
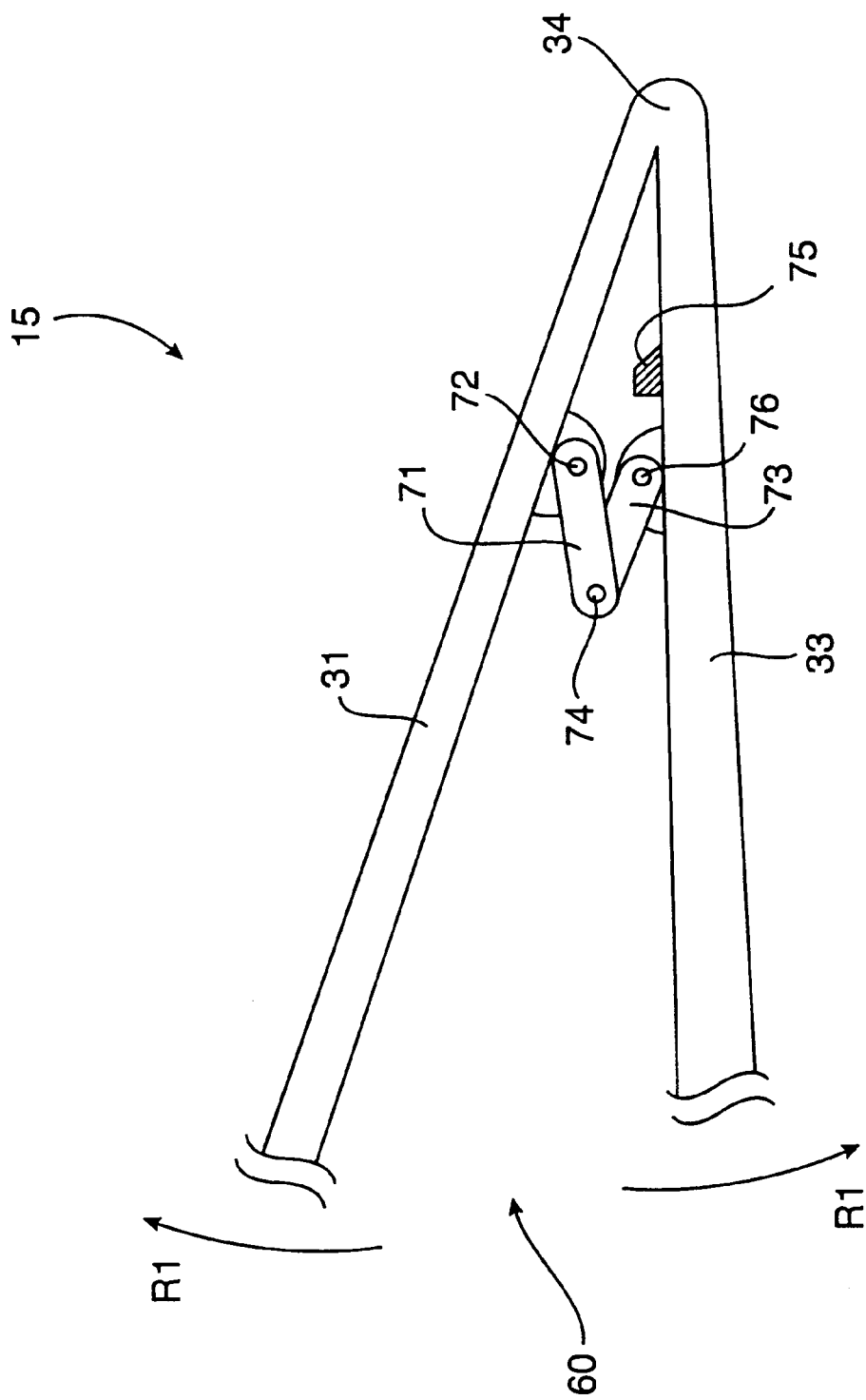
FIG. 6A illustrates systems for maintaining a cannula in a "locked open" state, with an enlarged portion of the cannula shown folded up.
Figure 6B:
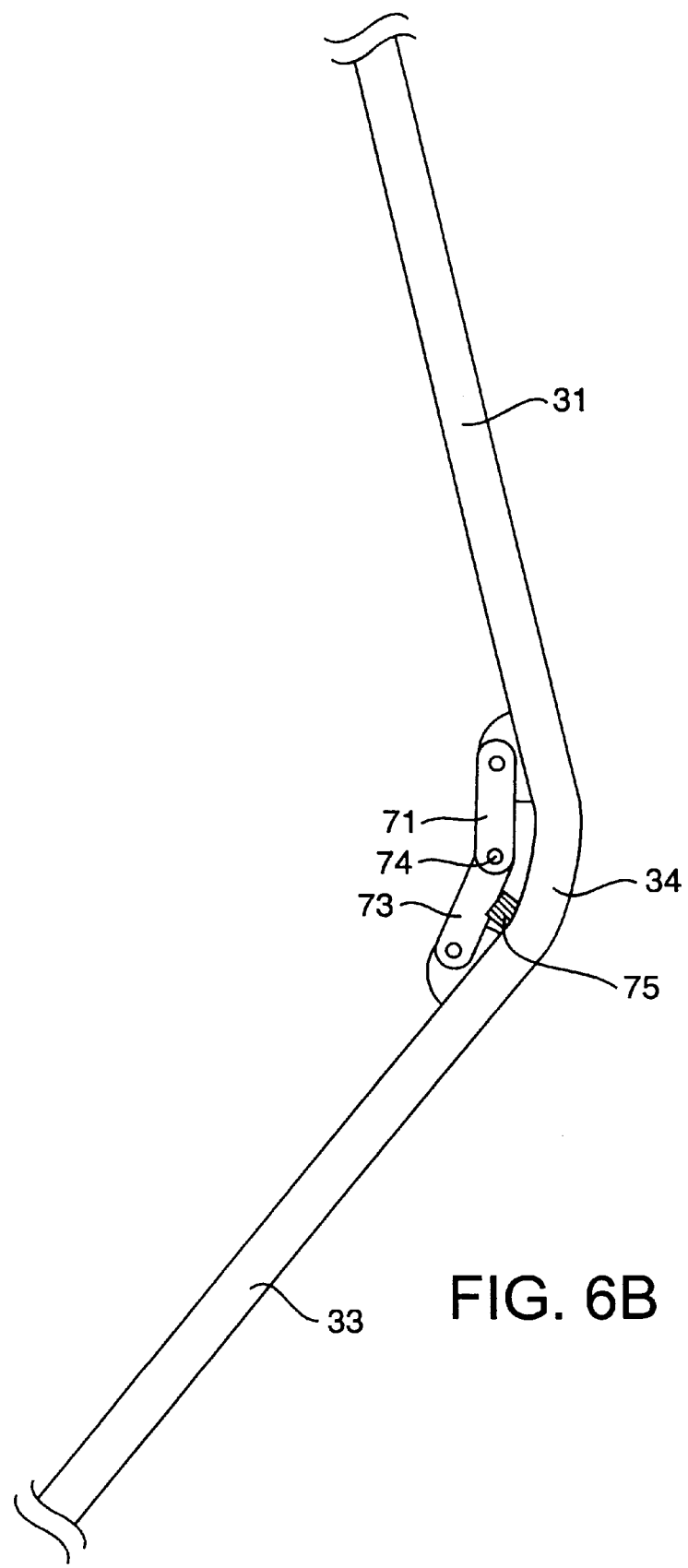
FIG. 6B illustrates systems for maintaining a cannula in a "locked open" state, with an enlarged portion of the cannula shown unfolded.

FIGS. 6A and 6B illustrate systems for maintaining the cannula in a "locked open" state. Referring first to FIG. 6A, an enlarged view of wall sections 31 and 33 is shown, (positioned in the same orientation as shown in FIG. IB). As cannula 15 is opened, with wall sections 31 and 33 moving in directions R1, hinges 71 and 73 will articulater around pins 72, 74 and 76, such that pin 74 moves radially outwardly toward hinge 34, until hinge 73 abuts stop 75 as shown in FIG. 6B. As can be appreciated from viewing FIG. 6B, hinge 73 pushing against stop 75 will hold hinge 34 on cannula 15 in a "locked open" position. In addition, the action of inserting an obturator through passageway 60 will assist in pushing pin 74 toward hinge 34 such that wall sections 31 and 33 remain locked open. As can be appreciated, a plurality of such locking system can be provided between some or all of the adjacent wall sections 20, 21, 22, 23, 30, 31, 32, 33, 40, 41, 42, 43, 50, 51, 52, and 53 such that each of the hinged connections between the wall sections (e.g.: hinges 24, 34, 44 and 54), can be kept open, supporting cannula 15 is a fully locked open position.

Figure 7A:
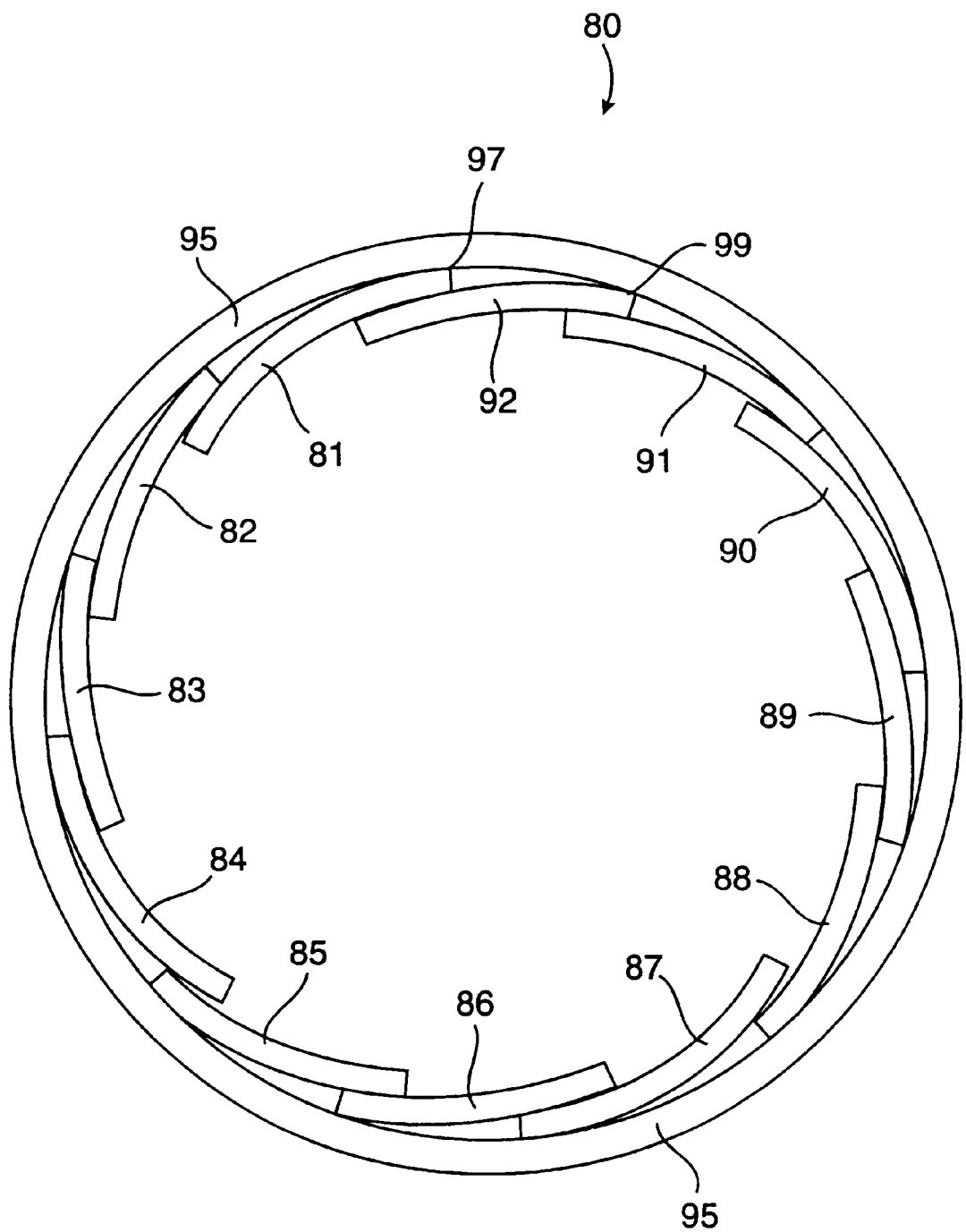
FIG. 7A illustrates a top sectional view of a second embodiment of the invention in an unexpanded position with the present cannula comprising a plurality of separate longitudinally extending wall sections disposed overlapping one on top of the other.
Figure 7B:
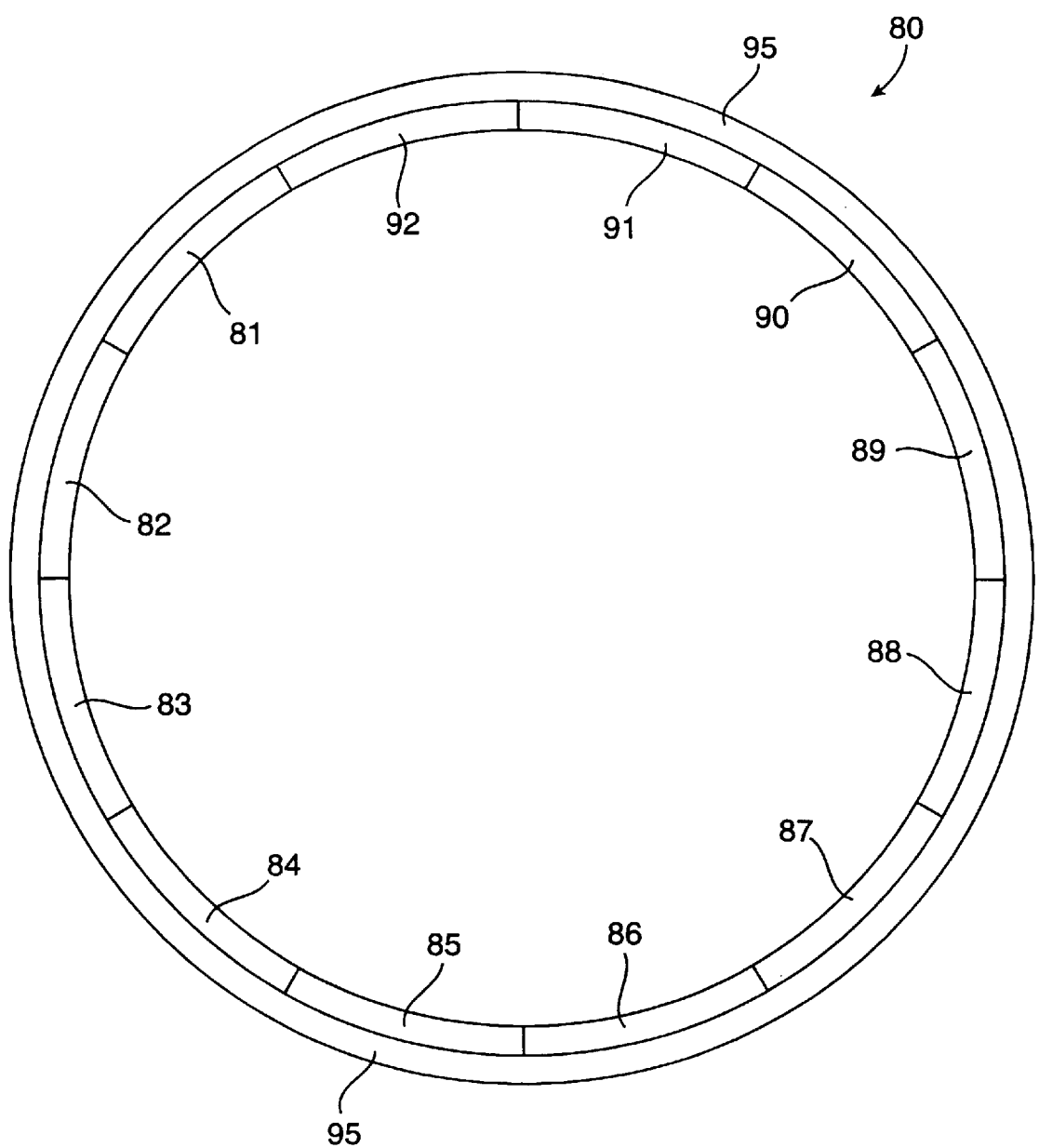
FIG. 7B illustrates a top sectional view of the invention of FIG. 7A in an expanded position with the plurality of separate longitudinally extending wall sections disposed adjacent one another.

FIGS. 7A and 7B show a second embodiment of the present invention in which cannula 80 comprises a plurality of wall sections 81, 82, 83, 84, 85, 86, 87, 88, 89, 90, 91 and 92, which may be either generally planar, or slightly curved as shown.

Wall sections 81, 82, 83, 84, 85, 86, 87, 88, 89, 90, 91 and 92, are preferably positioned to overlap one another, with at least some of the wall sections disposed on top of adjacent wall sections at one side, and beneath an opposite wall section when cannula 80 is unexpanded as shown in FIG. 7A. Wall sections 81, 82, 83, 84, 85, 86, 87, 88, 89, 90, 91 and 92 are received within an elastic sheath 95. In a preferred aspect, each of wall sections 81, 82, 83, 84, 85, 86, 87, 88, 89, 90, 91 and 92 may be attached at one end (e.g.: along side 97 for wall section 82 and along side 99 for wall section 92), to the interior of elastic sheath 95

After expansion to the state shown in FIG. 7B, (such as by inserting an obturator therethrough or inflating a balloon therein), wall sections 81, 82, 83, 84, 85, 86, 87, 88, 89, 90, 91 and 92 become disposed along their longitudinally extending sides buttressing against one another around the circumference of the cannula after the cannula has been expanded.

Figure 8A:
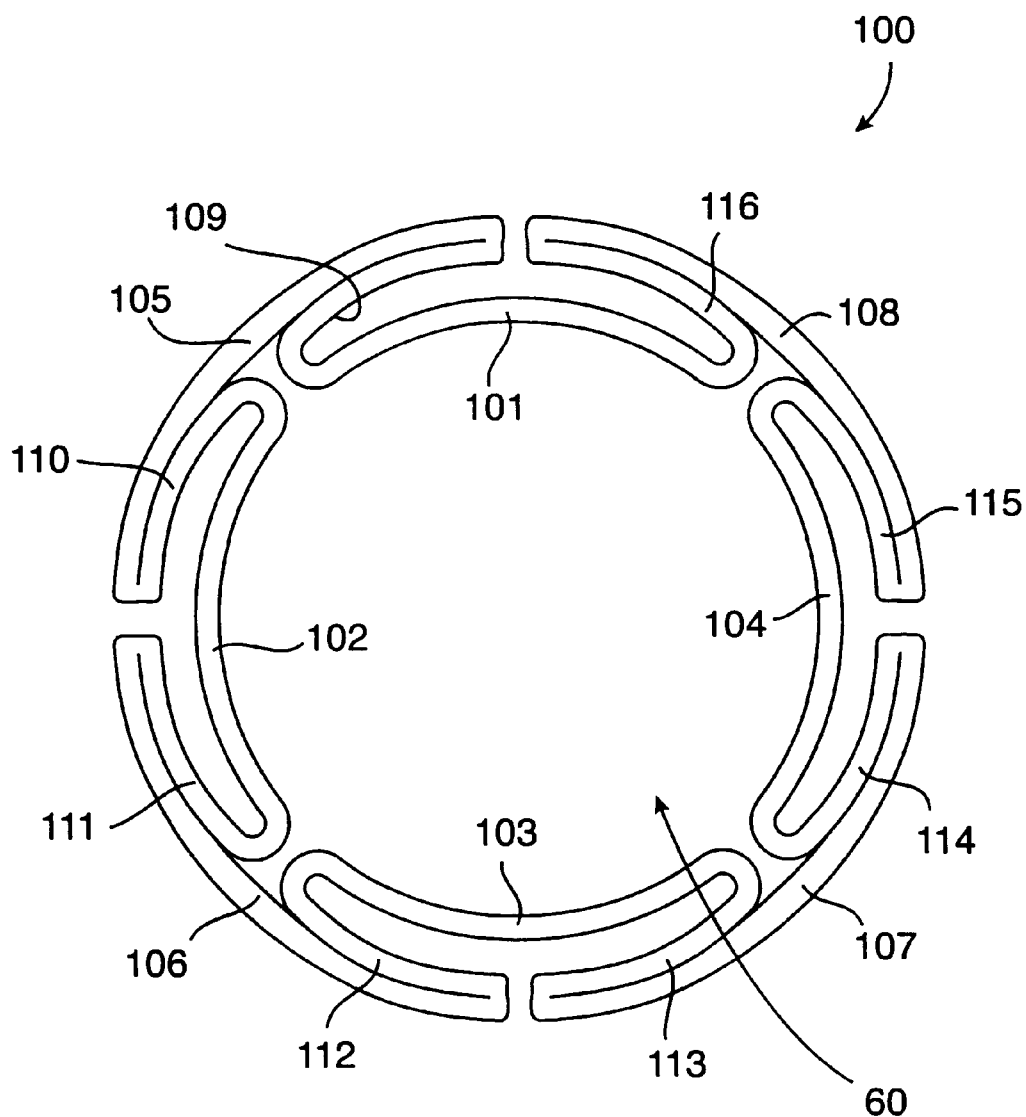
FIG. 8A illustrates a top sectional view of a third embodiment of the invention in an unexpanded position.
Figure 8B:
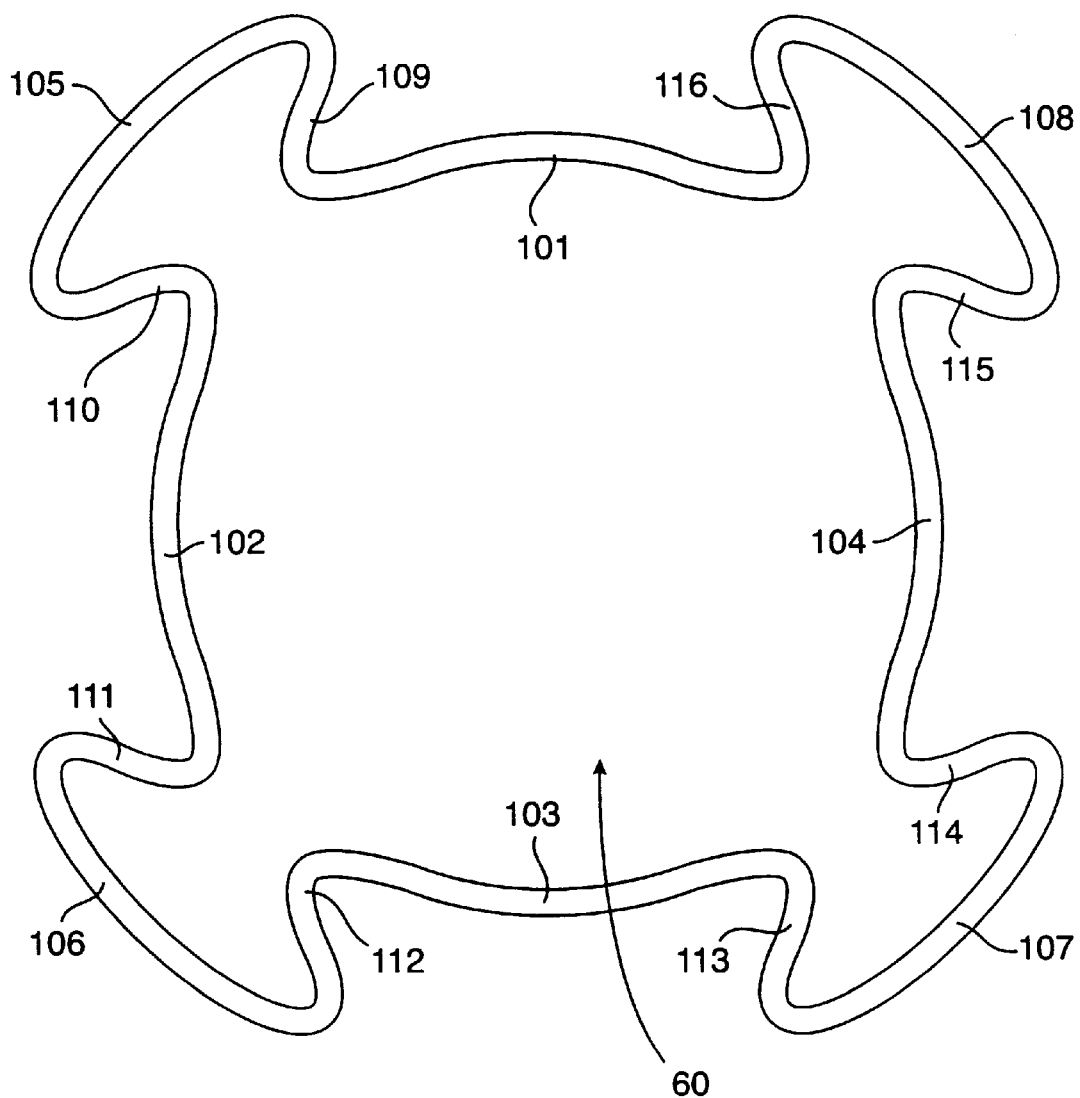
FIG. 8B illustrates a top sectional view of the invention of FIG. 8A in a partially expanded position.
Figure 8C:
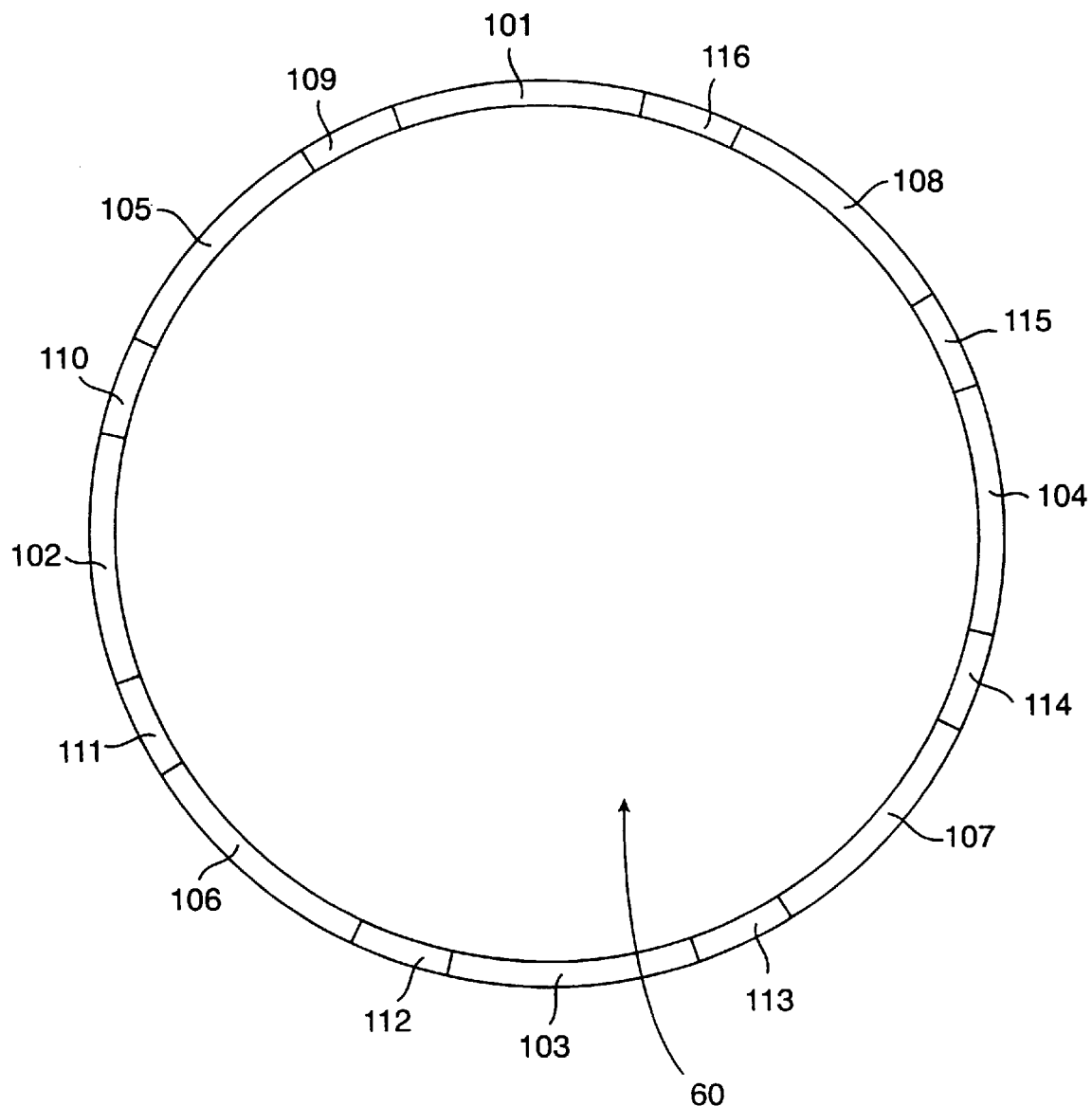
FIG. 8C illustrates a top sectional view of the invention of FIG. 8A in a fully expanded position.

FIGS. 8A, 8B and 8C shows a third embodiment of the present invention in which cannula 100 comprises a plurality of wall sections 101, 102, 103, 104, 105, 106, 107, 108, 109, 110, 111, 112, 113, 114, 115 and 116, initially folded together as shown. Wall sections 101, 102, 103, 104, 105, 106, 107, 108, 109, 110, 111, 112, 113, 114, 115 and 116 may be either generally planar, or slightly curved as shown.

Wall sections 101, 102, 103, 104, 105, 106, 107, 108, 109, 110, 111, 112, 113, 114, 115 and 116 are preferably positioned to overlap one another, wall sections 101, 102, 103 and 104 forming an interior surface with wall sections 105, 106, 107, and 108 forming an exterior surface.

After expansion to the state shown in FIG. 8C, (such as by inserting an obturator therethrough or inflating a balloon therein), wall sections 101, 102, 103, 104, 105, 106, 107, 108, 109, 110, 111, 112, 113, 114, 115 and 116 become disposed such that they wrap around the circumference of the cannula after the cannula has been expanded.

What is claimed is:

1. An expandable cannula comprising:
   an expandable elastic sheath; and
   a plurality of separate longitudinally extending wall sections disposed within the expandable elastic sheath, the separate longitudinally extending wall sections being initially deployed overlapping one another, with at least some of the wall sections disposed on top of adjacent wall sections at one side, and beneath an opposite wall section, at an opposite side when the elastic sheath is unexpanded; and wherein at least some of the wall sections are positioned with their longitudinally extending sides buttressing against one another around the circumference of the cannula after the elastic sheath has been expanded.

\* \* \* \* \*